(12) United States Patent
Mirowsky et al.

(10) Patent No.: US 6,372,131 B1
(45) Date of Patent: Apr. 16, 2002

(54) CLOSED COVER WASTE TREATMENT SYSTEM WITH IONIC OXYGEN GENERATOR

(76) Inventors: Bernard J. Mirowsky, 41 Sand Hill Rd., Annandale, NJ (US) 08801; Paul D. Mirowsky, 231 N. Union St., Lambertville, NJ (US) 08530

( * ) Notice: Subject to any disclaimer, the term of this patent is extended or adjusted under 35 U.S.C. 154(b) by 0 days.

(21) Appl. No.: 09/894,752

(22) Filed: Jun. 28, 2001

(51) Int. Cl.[7] .......................... B01D 53/34; A61L 9/03; A61L 9/22; C02F 1/24; C02F 1/00
(52) U.S. Cl. ................. 210/205; 210/218; 210/221.2; 210/916; 422/5; 423/219; 96/16; 96/52
(58) Field of Search .................. 210/218, 221.2, 210/916, 205; 422/5; 423/219; 96/16, 52

(56) References Cited

U.S. PATENT DOCUMENTS

| | | | |
|---|---|---|---|
| 4,550,010 A | * | 10/1985 | Chelu |
| 5,340,484 A | * | 8/1994 | Prince et al. |
| 5,501,844 A | | 3/1996 | Kasting, Jr. et al. |
| 5,913,809 A | | 6/1999 | Erlichman et al. |
| 6,071,418 A | | 6/2000 | Tai |
| 6,287,465 B1 | * | 9/2001 | Watanabe et al. |
| 6,315,893 B1 | * | 11/2001 | Sawada |

FOREIGN PATENT DOCUMENTS

| | | | |
|---|---|---|---|
| DE | 2410883 | * | 9/1975 |
| JP | 55-005775 | * | 6/1978 |
| JP | 54-002265 | * | 1/1979 |

* cited by examiner

*Primary Examiner*—Thomas M. Lithgow
(74) *Attorney, Agent, or Firm*—Kenneth P. Glynn, Esq.

(57) ABSTRACT

The present invention is a waste water treatment system, which includes at least one closed, covered structure having waste water ingress and waste water egress and waste water treatment capabilities within the structure, and having an ambient air ingress with predetermined volumetric air flow rates, and having an ambient air egress for release of air to the atmosphere; and further includes an ionic oxygen generator connected to the air ingress or egress and has sufficient capacity to generate at least 200 ions of ionic oxygen for removal of odor from exiting air before it is released to the atmosphere. In some preferred embodiments, the waste water treatment is a dissolved air flotation treatment with at least one covered tank containing solid-liquid waste content, and includes sufficient pumping capacity to floatate a solid component of the solid-liquid waste content of the tank.

20 Claims, 5 Drawing Sheets

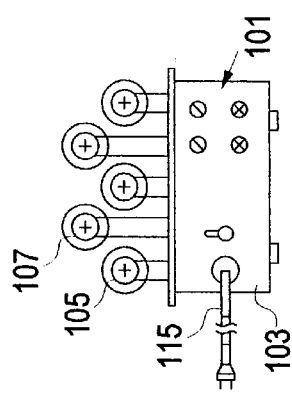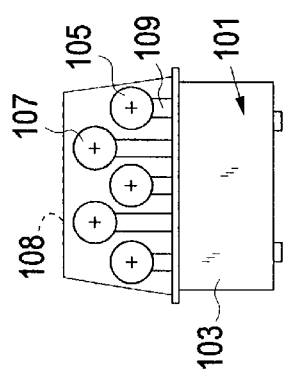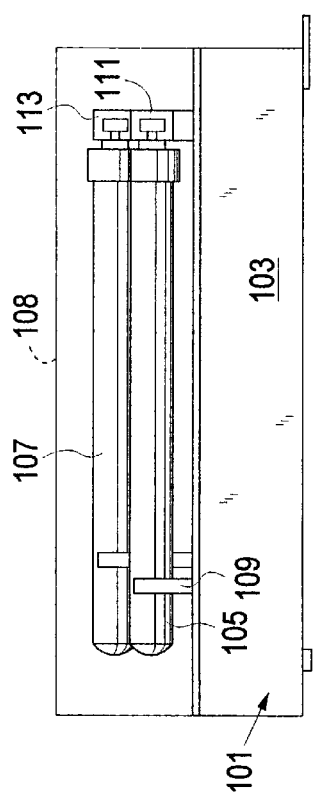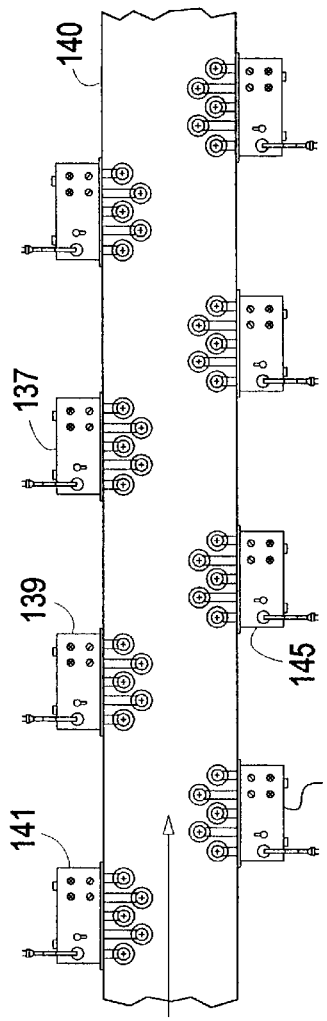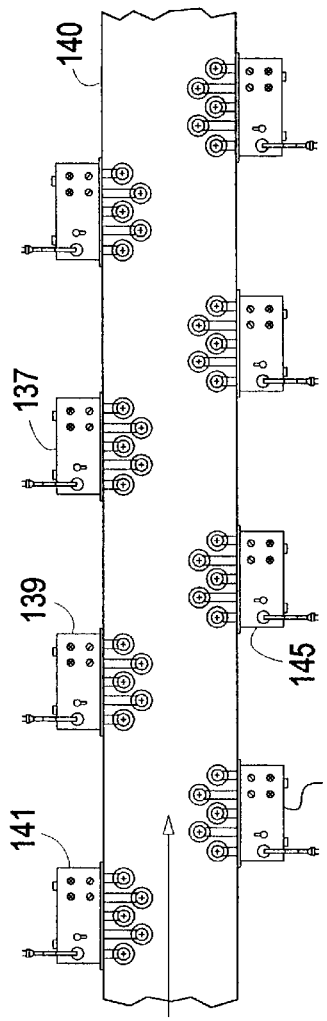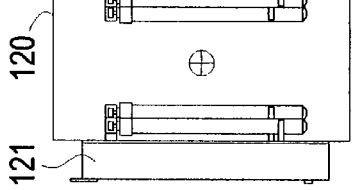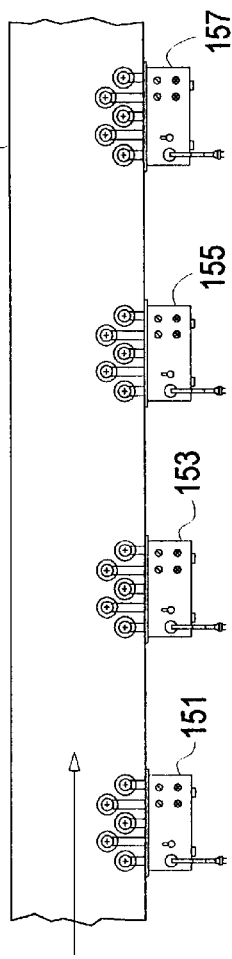

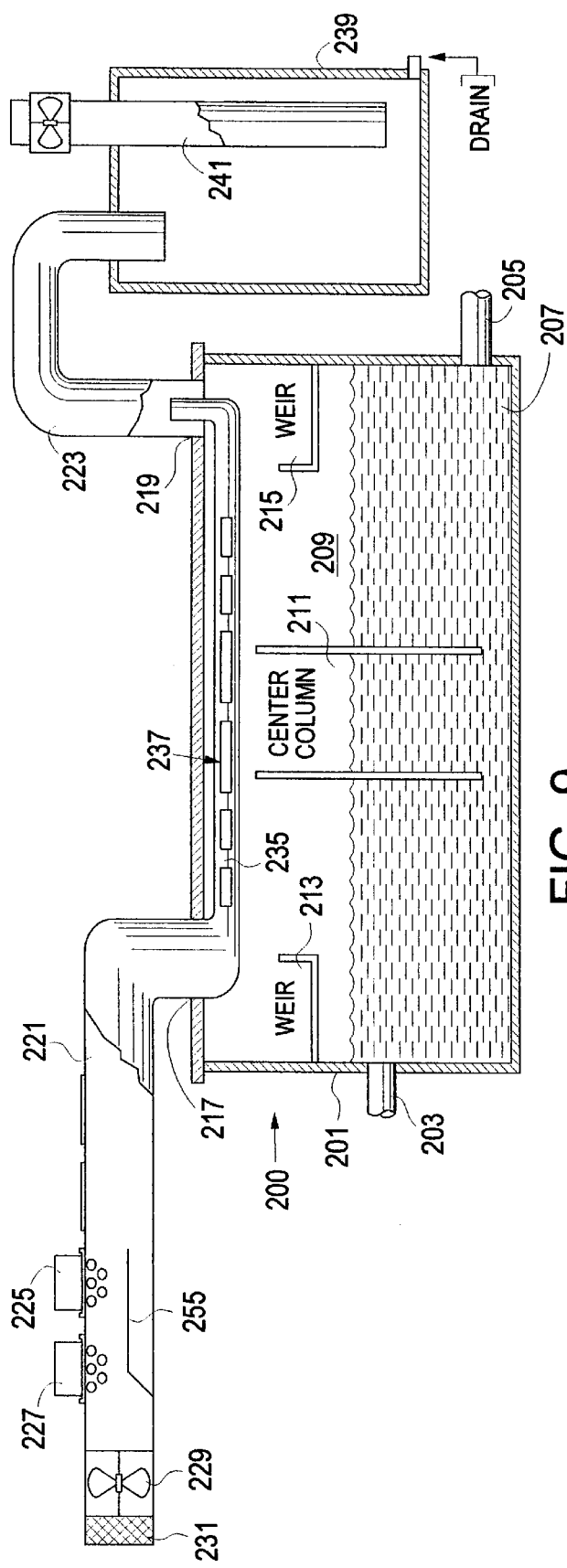
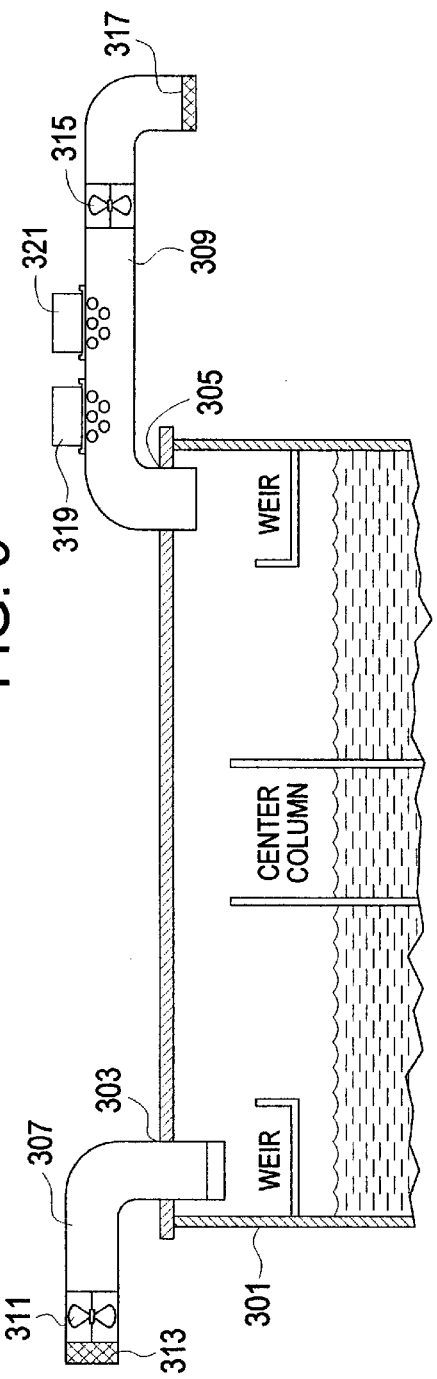
FIG. 9
FIG. 10

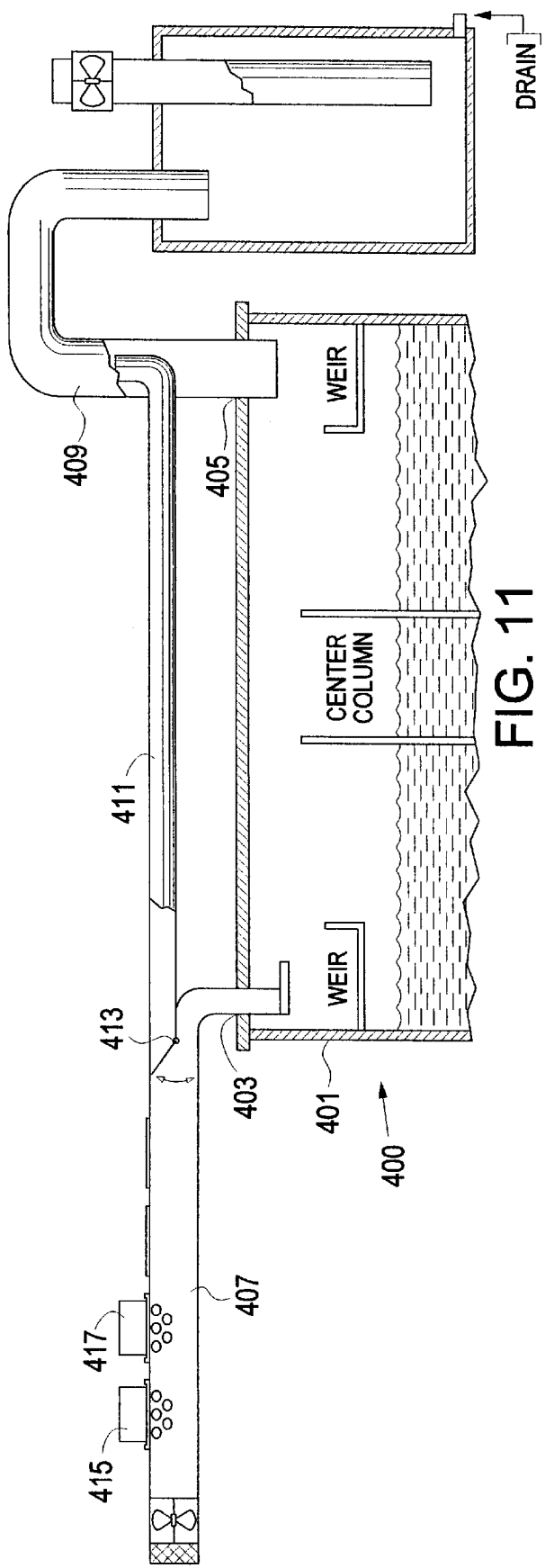
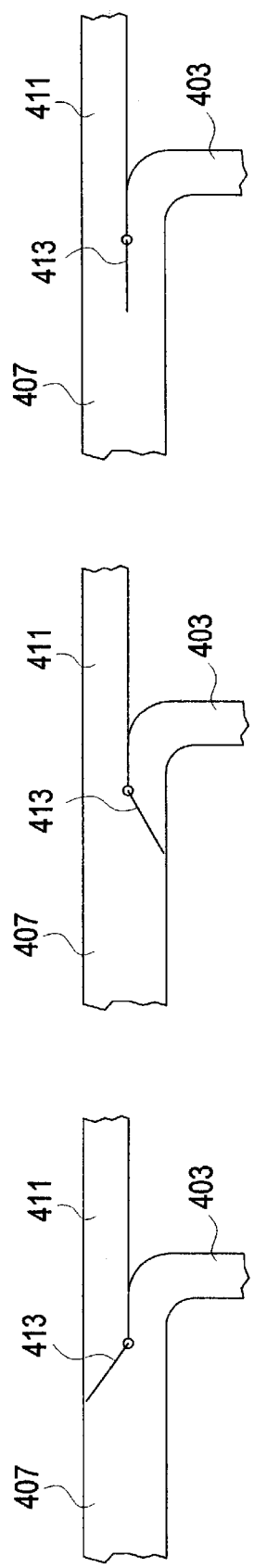
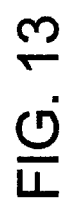
FIG. 11
FIG. 12
FIG. 13
FIG. 14

CLOSED COVER WASTE TREATMENT SYSTEM WITH IONIC OXYGEN GENERATOR

BACKGROUND OF THE INVENTION

1. Field of the Invention

The present invention is directed to waste treatment systems having odor problems, and, more specifically to waste treatment systems which may be adaptable to closed covers. These include waste water treatment systems for treatment of chemical processing waste water, systems for treatment of ammonia and/or ammonium compound-containing waste, and for treatment of animal and/or human waste treatment, such as dissolved air floatation treatment. The present invention systems are closed systems which include ionic oxygen generation and treatment of undesired odors with the generated ionic oxygen.

2. Information Disclosure Statement

The treatment of liquid and liquid-solid waste odors is typically either performed by the addition of chemicals to the waste, by scrubbing of effluents in some noxious environments, or by simple exhaust to the open atmosphere. In some situations, isolated ponding with evaporative removal has been utilized. However, closed covered systems using on-site generated ionic oxygen has not been used.

On the other hand, ionic oxygen generation has been available for removal of indoor air pollution, such as mold, bacteria and airborne viruses has been commercially available, but not within the system and manner described in the present invention.

The following United States Patents are of interest in that they illustrate waste water treatment methods and/or ozone generation, although the present invention does not rely upon ozone generation, but instead relies upon ionic oxygen generation:

U.S. Pat. No. 6,071,418 describes a method and system for wastewater treatment which describes and is particularly suitable for manure lagoons and pits. Specifically, an ozone gas is homogeneously distributed through an upper stratum of a contained liquid thereby creating an aerobic "cap", while still maintaining an anaerobic lower stratum. A perforated tube or plurality of tubes fixed within the upper stratum serves to distribute the ozone. Alternately, a buoyant vehicle propelled across the surface of the liquid may also serve to distribute the ozone and create the ozonated "cap". The vehicle provides an additional benefit of crust fragmentation and prevention thereby inhibiting and eliminating fly propagation, and hygienically improving lagoon or pit operation. In either embodiment, the ability to create an aerobic and anaerobic balance within the liquid facilitates a reduction in odor, a significant improvement of organic digestion and solids control, and a reduction in pathogens sometimes found in water recycled from the containment area.

U.S. Pat. No. 5,913,809 describes an ionization field which is produced across the pumped air flow to a fuel combustion process to increase the content of oxygen in the stream, and the stream reactivity. This ionization field may be produced between a sharp electrode and a grid or sheet, positioned in a shielded structure like the filter housing on the engine intake. Alternatively, an ultraviolet light source may be used to ionize the oxygen in the air stream. If either form the air stream may be compressed before its ionization and then may be injected into the exhaust products of the combustion process. The ionization power may be modulated along with the demand. Thus the throttle position may be sensed to modulate the voltage multiplier levels across the electrodes straddling the air stream, in accordance with the demand.

U.S. Pat. No. 5,501,844 describes an air treating apparatus which is a method therefore is disclosed that can be used in spaces occupied by humans or other mammals for deodorizing the air with ozone while the humans or other mammals are present. A housing having an air inlet and an air outlet defining an air flow passageway there between has a fan in the inlet for drawing air through the passageway and discharging the air through the outlet. The housing contains a transformer for supplying high voltage electrical power to an ozone generator in the air passageway for enriching the air in ozone and discharging a mixture of ozone in the air at a predetermined concentration. A potentiometer controls a timer for controlling the interval over which ozone is produced in an "on/off" manner. The time averaged concentration of ozone thereby is controlled so that exposure to ozone does not exceed established limits over time. Thus, notwithstanding the prior art, the present invention system is neither taught nor rendered obvious thereby.

SUMMARY OF THE INVENTION

The present invention is a waste treatment system, which includes the following:

(a.) at least one closed, covered structure having flowable waste content ingress and flowable waste content egress and waste treatment capabilities within the structure, and having an ambient air ingress with predetermined volumetric air flow rates, and having an ambient air egress for release of air to the atmosphere; and, (b.) an ionic oxygen generator connected to either the ambient air ingress or ambient air egress. A plurality of these generators could be included and could be located at or connected to either the ingress or egress, or one or more generators at both the ingress and egress.

The ionic oxygen generator is of sufficient capacity to generate at least 200 ions of ionic oxygen per cubic liter of incoming air, e.g. 1000 to 2500 ions of ionic oxygen per cubic liter, for removal of odor from exiting air before it is released to the atmosphere.

In some embodiments of the present invention, the closed, covered structure includes a cover which contains the ambient air ingress and ambient air egress, while in other situations, the air ingress and air egress may be in the structure or both the structure and the cover. Ambient air as used herein means air entering the structure from an outside source, and air exiting the structure with whatever additional content it may acquire while passing through the structure, such as ammonia or ammonium compounds, hydrogen sulfide and the like. The exact content of exiting ambient air is not critical to the present invention and such contents, as well as actual treatment details, are well known and are well within the skill of the artisan. The important feature is that the exiting air would have humanly detectable and possibly unhealthy odors and could be treated with ionic oxygen. Thus, the purpose of the present invention is to eliminate or substantially reduce such odors in a continuous, efficient and economic manner.

In some preferred embodiments, there is a cover and the ingress and egress may be located in the cover or elsewhere, but are advantageously located in the cover, especially in retrofitted systems where the structures, such as tanks, were previously uncovered.

In preferred embodiments of the present invention, the ambient air ingress and egress include an ingress channel and an egress channel, respectively, and there is further at least one air blower connected to the ingress channel and/or the egress channel. These channels may be constructed of any workable structures and materials, such as metal ductwork, metal, plastic, or glass tubing, or any other type of closed channel with open ends. However, in typical air blower/ circulation systems, metal ductwork is utilized and will suffice in the present invention.

The ionic oxygen generator is located at the ingress or egress, or near it, and may be located upstream or downstream from the ingress or egress, and in line with, but before or after one or more blowers.

In some embodiments, there is an external bypass channel connecting the ingress channel and the egress channel to one another and there is a valving mechanism which may be positioned either to permit ionic oxygen flow into the ingress and into the structure, or to permit ionic oxygen flow to bypass the ingress and the structure and to flow into the egress to thereby treat odors in exiting air before it is released to the atmosphere. In other embodiments, the valving mechanism includes a three way valve which may be positioned to either permit ionic oxygen flow into the ingress and into the structure, or to permit ionic oxygen flow to bypass the ingress and bypass the structure, and flow into the egress to thereby treat odors in exiting air before it is released to the atmosphere, or to do both simultaneously.

In other embodiments of the present invention, there is an internal channel connecting the ingress channel and the egress channel, and this internal channel includes at least one orifice located at some point on the internal channel within the structure so as to simultaneously permit ionic oxygen flow into the structure and into the egress channel, for simultaneous treatment of odor within the structure and of odor in exiting air in the egress channel before it is released to the atmosphere.

In some preferred embodiments, the waste treatment is waste water treatment and may include dissolved air flotation, e.g., with at least one covered tank containing solid-liquid waste content, and includes air pumps with sufficient pumping capacity to floatate a solid component of the solid-liquid waste content of one tank. Alternatively, a plurality of tanks or other vessels could be channel-interconnected with parallel, series, or both types of connections to create a matrix system with appropriate ionic oxygen generators strategically positioned to eliminate or substantially reduce odors.

BRIEF DESCRIPTION OF THE DRAWINGS

The present invention should be more fully understood when the specification herein is taken in conjunction with the drawings appended hereto wherein:

FIGS. 2, 3 and 4 show side, left end and right end views of one present invention system ionic oxygen generator with a plurality of plasma tubes;

FIGS. 5, 6, 7 and 8 show various channel and ionic oxygen generator arrangements which may be used in present invention systems;

FIG. 9 illustrates a present invention system which includes a bypass channel to permit in tank and in egress ionic oxygen treatment;

FIG. 10 shows a present invention system with ionic oxygen treatment in the egress channel only;

FIG. 11 illustrates a present invention system with an external bypass channel and valving options, while FIGS. 12, 13 and 14 show different valve positions; and, FIG. 15 shows a present invention system with a central egress housing unit with baffling for intermixing exit gases and ionic oxygen.

DETAILED DESCRIPTION OF THE PRESENT INVENTION

Figure 1:
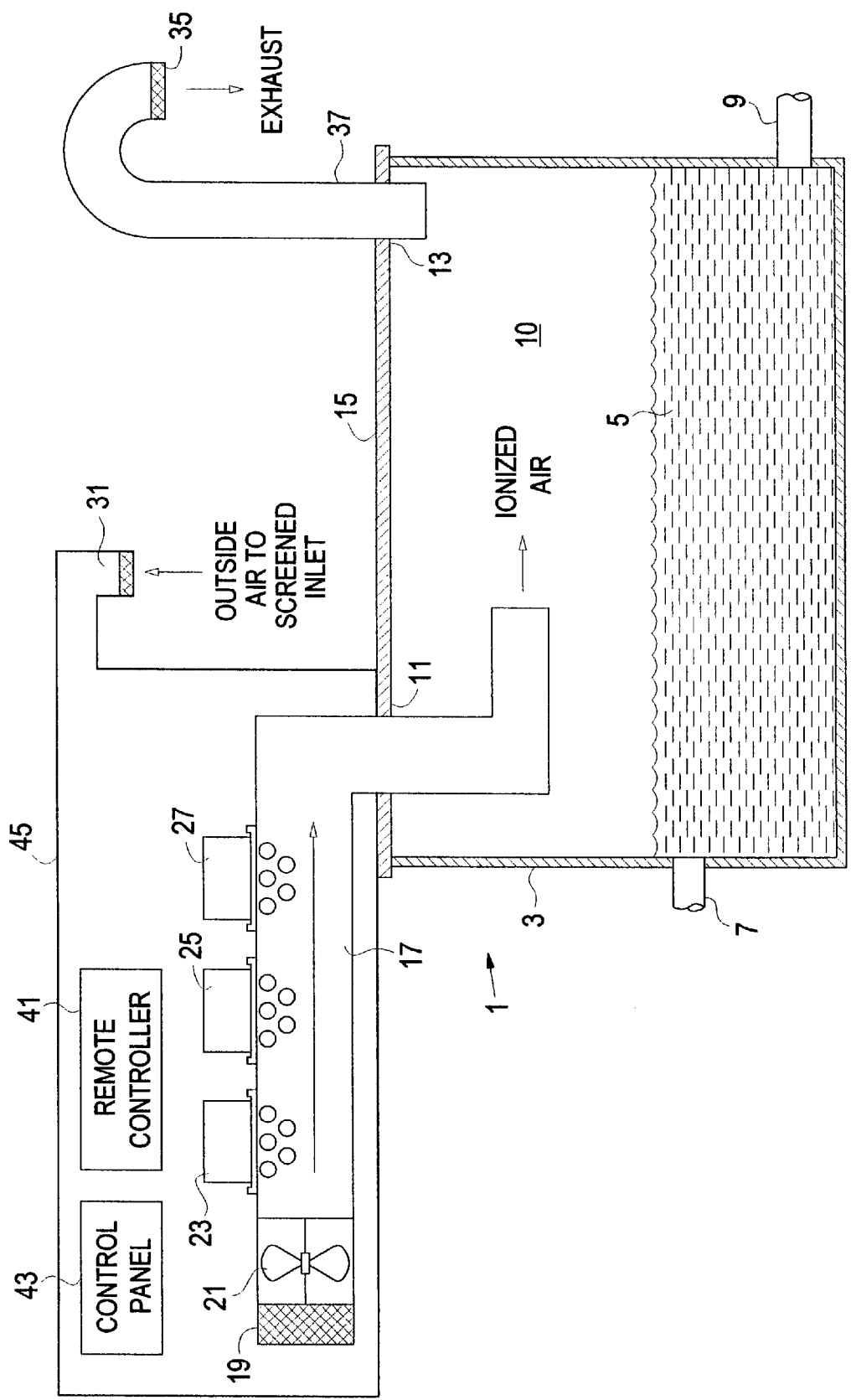
FIG. 1 illustrates a front view of one embodiment of the present invention system.

The present invention is shown in a first embodiment in FIG. 1, wherein the system 1 includes a closed, covered waste treatment structure 3, with waste water ingress 7 and waste water egress 9. The structure 3 may be a circular tank, a rectangular reaction vessel, a sludge treatment tank or any other closed structure of any geometric configuration and content which contains odors treatable with ionic oxygen.

In FIG. 1, the structure 3 has a cover 15 and contains liquid (or slurry or solid-liquid content or the like), including flowable content 5, and odorous gas and air 10. Cover 15 also contains ambient air ingress 11 and ambient air egress 13, as well. as ingress channel 17 and egress channel 37, typically ductwork, and arranged as shown in the Figure.

In FIG. 1, the ingress channel 17 has a plurality of ionic oxygen generators 23, 25 and 27, as well as fan 21 and intake filter 19. The fan 21 and the aforesaid ionic oxygen generators are operated by control panel 43 and remote controller 41. Optional external housing 45 protects the system components from severe weather, etc. and includes an outside air inlet 31 with screen. Ambient air enters inlet 31 and then enters filter 19 as drawn by fan 21 and enters channel 17 where the ionic oxygen generated therein is mixed with it and reacts with gases in air 10 to oxidize and remove odors. the mixture exits through channel 37 to the outside environment in a low to undiscernible odor level.

FIG. 2 shows a side view, FIG. 3 shows a left end view, and FIG. 4 shows a right end view of a present invention system ionic oxygen generator 101. Ionic oxygen generator 101 contains a plurality of individual ionization tubes such a tubes 105 and 107. They have supports such as support 109 along with connectors such as connectors 111 and 113 which elevate the tubes so as to provide 360 degree exposure to the atmosphere. The power generator is contained within housing 103 to operate on 110/220 volts alternating current at a power consumption based on the number of tubes and the size of the tubes. For example, in this case, using five tubes, the consumption would be at about 40 watts. There is an open gridwork cover 108 (shown in FIGS. 2 and 3 only). Ionic oxygen generator 101 and similar devices are specifically designed to create measurable and controllable quantity of negative and positive ions. These activate the oxygen molecules in the air with uneven polarity and form clusters of 15 to 60 molecules which raise the airs electrical potential. This enables the generated ionic oxygen to oxidize odorous volatile gases. Thus, odors, especially of organic origin such as animal or human waste, are quickly eliminated. In addition to odors of organic origin and inorganic gases generated therefrom, such as hydrogen sulfide and other sulfur byproducts, the ionic oxygen clusters generated within the present invention may include one or more acetylaldehyde, acrylic acid, ammonia, aniline, benzene, carbon dioxide, carbon monoxide, diethylamine, ethylacrylat, formaldehyde, furfuraldehyde, kresol, methane, methylamine, phenol, sulfur dioxide, sulfur carbon, toluol, vinegar acid, xylol and many other odorous gases.

These ionic oxygen generators are reactive plasma generators which produce ionic oxygen instead of ozone at a rate of over 100,000 ions per cubic centimeter. Although ozone is a byproduct of this ionization process, very minute parts of ozone such as less than 0.015 parts per million. In fact, these ionic oxygen generators have reduced ozone levels from 300% in excess of the United States Protection Agency standards by 300% down to no detectable ozone, in dragger tube airline tests.

FIG. 5 shows a top cut front view into a vertical duckwork 120. It shows the orientation and position of staggered ionic oxygen generators 121 and 123 on each side.

FIG. 6 shows a cut end view of a plenum box 130 with ionic oxygen generators 131, 133 and 135 arranged on the sides and top for a horizontal flow configuration.

FIG. 7 shows a side cut view of horizontal duckwork 140 with a plurality of ionic oxygen generators arranged in staggered, opposing positions. Thus, typical are ionic oxygen generators 137, 139 and 141 located in the top and 143 and 145 located in the bottom. An alternative arrangement would be to have the generators located on the sides or only on the top or bottom. FIG. 8 shows ionic oxygen generators 151, 153, 155 and 157 located in the bottom of tubing channel 150.

The present invention is shown in an alternative embodiment in FIG. 9, wherein the system 200 includes a closed, covered waste treatment structure, in this case, tank 201, with flowable waste ingress 203 and waste egress 205. Tank 201 may be a circular tank, a rectangular reaction vessel tank or the like and may contain waste water or organic or chemical flowable waste which contains odors treatable with ionic oxygen.

In FIG. 9, the tank 201 has a cover 210 and contains liquid (or slurry or solid-liquid content or the like), including flowable content 207, and odorous gas and air 209. Cover 210 also contains ambient air ingress 217 and ambient air egress 219, as well as ingress channel 221 and egress channel 223, typically ductwork, and arranged as shown in the Figure.

In FIG. 9, there is also an internal bypass channel 235 which connects from ingress channel 221 to egress channel 223, and contains vent orifices, such as orifice 237, for flow of generated ionic oxygen into tank 201 to directly treat odors 209, as well as treat effluents in egress channel 223 at the exit end of bypass channel 235.

As seen in FIG. 9, ingress channel 221 has a plurality of ionic oxygen generators 225 and 227, as well as fan 229 and intake filter 231. The fan 229 and the aforesaid ionic oxygen generators are operated by a control panel similar to that shown in FIG. 1. There is also an effluent after tank unit 239 for increased hold time for ionic oxygen interaction, with ultimate exhaust and auxiliary fan 241, as shown. When ambient air enters inlet channel 221, it is constricted at baffle 255 to increase velocity at the ionic oxygen generators to optimize the ions per cubic liter entering the system downstream.

FIG. 10 shows another present system wherein the system is similar to that shown in FIG. 9, except that the ionic oxygen geenerators are located in the egress channel and there is no bypass channel. Here, tank 301 has an ingress 303 with ingress channel 307, which contains fan 311 and filter 313. Cover 310 also contains egress 305 and egress channel 309, which contains fan 315 and filter 317, as well as ionic oxygen generators 319 and 321, to treat odorous effluents before exiting the system. Additionally, effluent after tank 239 of FIG. 9 may optionally be included.

FIG. 11 shows another present system wherein the system is similar to that shown in FIG. 9, except that the bypass channel is an external bypass channel. Thus, the system of FIG. 9 has simultaneous in-tank and post tank mixing of ionic oxygen and odorous gases, whereas this system of FIG. 11 presents an either/or situation. Here, system 400 includes tank 401 with an ingress 403 with ingress channel 407, which contains a fan and filter, as well as ionic oxygen generators 415 and 417. External bypass channel 411 connects channels 407 and 409.

A valving mechanism 413 controls flow into the system and reference is made to FIGS. 11, 12, 13 and 14 taken together, wherein identical parts are identically numbered. When the valve flap is up, as shown in FIG. 12, ionic oxygen flows only to the tank. When it is down, as in FIG. 13, ionic oxygen flows only through the external bypass to treat effluents. When it is in the middle position shown in FIG. 14, ionic oxygen flows in both channels.

Figure 15:
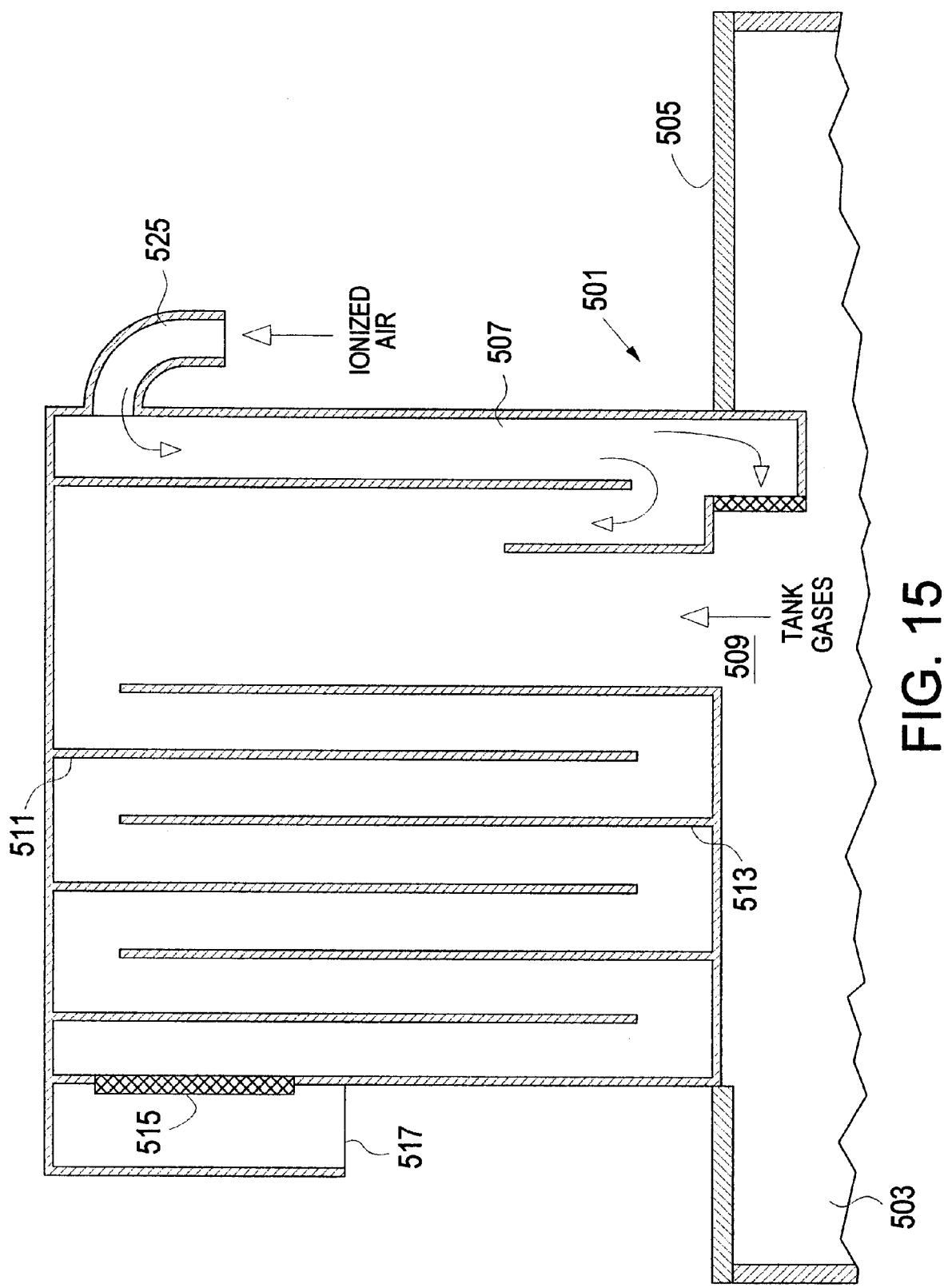

FIG. 15 shows a present invention system 501 and a closed structure 503 with a central housing 507 with egress 509, air ingress being through a below-liquid level aerator, for example, not shown. Housing 507 includes an ionic oxygen inlet 505 from generators (not shown), which intermixes with exiting tank gases. Baffles, such as 511 and 513, act to aid in intermixing to increase efficiency and increase odorous gas oxidation. The resulting treated air exits through filter 515 and exhaust 517.

Obviously, numerous modifications and variations of the present invention are possible in light of the above teachings. It is therefore understood that within the scope of the appended claims, the invention may be practiced otherwise than as specifically described herein.

What is claimed is:

1. A flowable waste treatment system, which comprises:
   (a.) at least one closed, covered structure having flowable waste ingress and flowable waste egress and waste treatment means within said at least one structure, and having an ambient air ingress with predetermined volumetric air flow rates, and having an ambient air egress for release of air to the atmosphere; and,
   (b.) an ionic oxygen generator connected to one of said ambient air ingress and ambient air egress, said ionic oxygen generator being of sufficient capacity to generate at least 200 ions of ionic oxygen per cubic liter of incoming air for removal of odor from exiting air before it is released to the atmosphere.

2. The system of claim 1 wherein said ambient air ingress includes an ingress channel of ductwork from an outside environment into said enclosed structure and said ionic generator is located within said ductwork.

3. The system of claim 1 wherein said ambient air ingress includes at least one air blower connected thereto.

4. The system of claim 1 wherein said covered structure includes a cover which contains said ambient air ingress and said ambient air egress.

5. The system of claim 4 wherein said cover ambient air ingress and egress include an ingress channel and an egress channel, respectively, and there is further at least one air blower connected to at least one of said ingress channel and said egress channel.

6. The system of claim 5 wherein said ionic oxygen generator is located within said ingress channel.

7. The system of claim 6 wherein there is an external bypass channel connecting said ingress channel and said egress channel to one another and there is a valving mechanism either to permit ionic oxygen flow into said ingress and into said structure, or to permit ionic oxygen flow to bypass said ingress and said structure and flow into said egress to thereby treat odors in exiting air before it is released to the atmosphere.

8. The system of claim 6 wherein there is an external bypass channel connecting said ingress channel and said egress channel to one another and there is a valving mechanism either to permit ionic oxygen flow into said ingress and into said structure, or to permit ionic oxygen flow to bypass said ingress and said structure and flow into said egress to thereby treat odors in exiting air before it is released to the atmosphere, or both simultaneously.

9. The system of claim 6 wherein there is an internal channel connecting said ingress channel and said egress channel, said internal channel including at least one orifice located within said structure so as to simultaneously permit ionic oxygen flow into said structure and into said egress channel, for treatment of odor within said structure and of odor in exiting air in said egress channel before it is released to the atmosphere.

10. The system of claim 5 wherein said ionic oxygen generator is located within said egress channel.

11. The system of claim 1 wherein said waste water treatment means includes dissolved air flotation means with at least one covered tank containing solid-liquid waste content, and includes pumping means with sufficient pumping capacity to floatate a solid component of the solid-liquid waste content of said at least one tank.

12. The system of claim 11 wherein said ambient air ingress includes an ingress channel of ductwork from an outside environment into said enclosed structure and said ionic generator is located within said ductwork.

13. The system of claim 11 wherein said ambient air ingress includes at least one air blower connected thereto.

14. The system of claim 11 wherein said covered structure includes a cover which contains said ambient air ingress and said ambient air egress.

15. The system of claim 14 wherein said cover ambient air ingress and egress include an ingress channel and an egress channel, respectively, and there is further at least one air blower connected to at least one of said ingress channel and said egress channel.

16. The system of claim 15 wherein said ionic oxygen generator is located within said ingress channel.

17. The system of claim 16 wherein there is an external bypass channel connecting said ingress channel and said egress channel to one another and there is a valving mechanism either to permit ionic oxygen flow into said ingress and into said structure, or to permit ionic oxygen flow to bypass said ingress and said structure and flow into said egress to thereby treat odors in exiting air before it is released to the atmosphere.

18. The system of claim 16 wherein there is an external bypass channel connecting said ingress channel and said egress channel to one another and there is a valving mechanism either to permit ionic oxygen flow into said ingress and into said structure, or to permit ionic oxygen flow to bypass said ingress and said structure and flow into said egress to thereby treat odors in exiting air before it is released to the atmosphere, or both simultaneously.

19. The system of claim 16 wherein there is an internal channel connecting said ingress channel and said egress channel, said internal channel including at least one orifice located within said structure so as to simultaneously permit ionic oxygen flow into said structure and into said egress channel, for treatment of odor within said structure and of odor in exiting air in said egress channel before it is released to the atmosphere.

20. The system of claim 15 wherein said ionic oxygen generator is located within said egress channel.

* * * * *